US00PP13477P2

(12) United States Plant Patent
Slaughter et al.

(10) Patent No.: US PP13,477 P2
(45) Date of Patent: Jan. 14, 2003

(54) NECTARINE TREE NAMED 'BURNECTFOUR'

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/027,862

(22) Filed: Dec. 19, 2001

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of nectarine tree substantially as illustrated and described and which produces an attractively colored yellow-fleshed clingstone nectarine which is mature for harvesting and shipment approximately September 8 to September 18 under the ecological conditions prevailing in the San Joaquin Valley of Central California.

1 Drawing Sheet

BACKGROUND OF THE NEW VARIETY

Botanical Classification: *Prunus persica.*
Variety Denominaton: 'BURNECTFOUR'.

The present invention relates to a new, novel and distinct variety of nectarine tree, *Prunus persica* var. (*nucipersica*), which has been denominated varietally as 'Burnectfour'. The present variety of nectarine tree resulted from an on-going program of fruit and nut tree breeding. The purpose of this program is to improve the commercial quality of deciduous fruit and nut varieties and rootstocks by creating and releasing promising selections of prunus, malus and regia species. To this end we make both controlled and hybrid cross pollinations each year in order to produce seedling populations from which improved progenies are evaluated and selected.

The seedling 'Burnectfour' was originated by us from a population of seedlings grown in our experimental orchards located near Fowler, Calif. The seedlings, grown on their own roots, were the result of a controlled cross of the nectarine tree 'September Red' (U.S. Plant Pat. No. 5,664) used as the seed parent, and the nectarine tree 'Spring Bright' (U.S. Plant Pat. No. 7,507) which was used as the pollen parent. One seedling, which is the present variety, exhibited especially desirable characteristics and was marked for subsequent observation. After the 1996 season, the new, present variety was selected for advanced evaluation and repropagation.

ASEXUAL REPRODUCTION

Asexual reproduction of the new and distinct variety of nectarine tree was made by budding same to 'Nemaguard' Rootstock (non-patented). This was performed by us in our experimental orchard located near Fowler, Calif. Subsequent evaluations have shown that those asexual reproductions run true to the original tree. All characteristics of the original tree and its fruit were established and appeared to be transmitted through succeeding asexual propagations.

SUMMARY OF THE VARIETY

'Burnectfour' is a new and distinct variety of nectarine tree, which is of medium to large size, has vigorous growth, and is a regular and productive bearer of large, firm, yellow flesh, semi-freestone fruit with good flavor and eating quality. The tree has a medium-chilling requirement of approximately 600 hours. The tree also produces relatively uniformly sized fruit throughout the tree, with a high degree of red color, and firm flesh. The fruit appears to have good handling and shipping quality. The 'Burnectfour' nectarine tree bears fruit that is ripe for commercial harvesting and shipment on approximately September 8 to September 18 under ecological conditions prevailing in central California. In comparison to the parent 'September Red' Nectarine (U.S. Plant Pat No. 5,664), the new variety ripens 10 or more days later.

BRIEF DESCRIPTION OF THE DRAWING

The accompanying drawing shows two whole fruit; a half fruit with the pit exposed revealing an equatorial (ventral view); one vegetative shoot with typical leaves and one pit. Two of the fruit show their external coloration sufficiently matured for harvesting and shipment. The colors are as nearly true as is reasonably possible in a color photographic representation of this type. Due to chemical development, processing and printing of the photographic image, the leaves, pit and fruit depicted in this photograph may or may not be accurate when compared to the actual botanical specimen. For this reason, future color references should be made to the color plates (Royal Horticultural Society) and descriptions provided hereinafter.

DETAILED DESCRIPTION

Referring more specifically to the pomological details of this new and distinct variety of nectarine tree, the following has been observed during the fifth fruiting season under the ecological conditions prevailing at the orchards located near the town of Fowler, county of Fresno, state of California. All major color code designations are by reference to The R.H.S. Colour Chart (Fourth Edition) provided by The Royal Horticultural Society of Great Britain.

Tree:

*Size.*—Generally. — Considered medium as compared to other common commercial nectarine cultivars ripening in the mid season of maturity. The tree was pruned to a height of about 304.8 cm to about 365.7 cm at maturity.

*Vigor.*—Moderately vigorous. The variety grew from about 131.92 cm to 192.8 cm in height the first growing season. The variety was pruned to a height of about 106.7 cm during the first dormant season and primary scaffolds were then selected for the desired tree structure.

*Productivity.*—Considered productive.

*Bearer.*—Regular. Fruit set has been heavy and thinning was necessary during the past 4 years.

*Form.*—Upright, and pruned to a vase shape.

*Density.*—Medium dense. It has been discovered that pruning the branches from the center of the tree to obtain a vase shape allows for air movement and sunlight to enhance fruit color and renewal of fruiting wood throughout the tree.

*Hardiness.*—The present tree was grown and evaluated in USDA Hardiness Zone 9. Winter chilling requirements for this tree are approximately 600 hours below 7.0 degrees C. The variety was considered hardy under typical Central San Joaquin Valley conditions.

Trunk:

*Diameter.*—Approximately 17.0 cm in diameter when measured at a distance of approximately 15.24 cm above the soil level, at the end of the fifth growing season.

*Bark texture.*—Considered moderately rough with numerous folds of papery scarfskin being present.

*Lenticels.*—Numerous flat, oval lenticels are present. The lenticels range in size in size from approximately 2.0 to 5.0 millimeters in width, and from 1 to 2 millimeters in height.

*Lenticel color.*—Considered an Orange Brown. (RHS Greyed-Orange N172 A). Bark Coloration. — Variable, but it is generally considered to be a grey-brown (RHS Greyed-Orange Group 177 A.

Branches:

*Size.*—Considered medium for the variety.

*Diameter.*—Average as compared to other varieties. The branches have a diameter of about 80.0 millimeters when measured during the fifth year after grafting.

*Surface texture.*—Average, and appearing furrowed on wood which is several years old.

*Crotch angles.*—Primary branches considered variable between about 45 to 49 degrees from the horizontal axis. This characteristic is not distinctive of the variety, however.

*Current season shoots.*—Surface texture — Substantially glabrous.

*Internode length.*—Approximatley 2.3 to 2.4 cm.

*Color of mature branches.*—Medium brown, (RHS Grey Brown Group N199 C).

*Current seasons shoots.*—Color. — Light green, (RHS Yellow Green Group 144 C). The color of new shoot tips is considered a bright and shiny green (RHS Green Group 134 C).

Leaves:

*Size.*—Considered medium for the species. Leaf measurements have been taken from vigorous upright current growth at approximately mid-shoot.

*Leaf length.*—Approximately 140 to 170 millimeters.

*Leaf width.*—Approximately 36 to 43 millimeters.

*Leaf base shape.*—Slightly oblique relative to the leaf longitudinal axis.

*Leaf form.*—Lancelolate.

*Leaf tip form.*—Acuminate.

*Leaf color.*—Dark green, (RHS Yellow Green Group 146 B).

*Leaf texture.*—Glabrous.

*Lower surface.*—Medium green, (RHS Yellow-Green Group 145 A).

*Leaf venation.*—Pinnately veined.

*Mid-vein.*—Color. — Light yellow green, (RHS Yellow Green Group 145 D).

*Leaf margins.*—Slightly undulating. Form. — Considered crenate, occasionally doubly crenate. Uniformity. — Considered generally uniform.

*Leaf petioles.*—Size. — Considered medium long to long. Length. — 9.0 mm to about 12.0 mm. Diameter. — 1.5 mm to about 2.5 mm. Color. — Pale green, (RHS Yellow Green Group 145 D).

*Leaf glands.*—Size. — 1.0 mm in height and about 1.0 to 2.0 mm in width. Numbers. — Generally one per side, occasionally two per side. Type. — Globose, and considered reasonably unappressed to the petiole margin. Color. — Greenish brown (RHS Yellow Green Group152 B).

*Leaf stipules.*—Size. — Medium large for the variety. Number. — Typically 2 per leaf bud, and up to 6 per shoot tip. Form. — Lanceolate in form, and having a serrated margin. Color. — Green (RHS Green Group 132 A) when young but graduating to a yellow-brown color (RHS Grey Orange group 177 A) with advancing senescence. The stipules are considered to be early deciduous.

Flowers:

*Flower buds.*—Generally — The floral buds are considered to be large, about 15 millimeters wide, and about 21 millimeters long; conic in form; and slightly appressed relative to the bearing shoot.

*Flower buds.*—Color — The bud scales are gray-brown, (approximately RHS Greyed Purple Group 183 A). The buds are considered hardy under typical central San Joaquin Valley climatic conditions.

*Hardiness.*—No winter injury has been noted during the last several years of evaluation in The Central San Joaquin Valley. The current variety has not been intentionally subjected to drought or heat stress and therefore this information is not available.

*Date of first bloom.*—Feb. 22, 2000.

*Blooming time.*—Considered early in relative comparison to other commercial nectarine cultivars grown in the Central San Joaquin Valley. The date of full bloom was observed on Mar. 2, 2000. The date of bloom varies with climatic conditions.

*Duration of bloom.*—Approximately 8 days.

*Flowers type.*—The variety is considered to have a showy type flower.

*Flower size.*—Flower diameter at full is approximately 31.0 to 36.0 millimeters.

*Bloom quantity.*—Considered abundant.

*Flower bud frequency.*—Normally 1 to 2 appear per node.

*Petal size.*—Generally — Considered medium large to large for the species. Length. — Approximately 16.0 to 19.0 millimeters. Width. — Approximately 17.0 to 19.0 millimeters.

*Petal form.*—Broadly ovate.

*Petal count.*—Nearly always 5.

*Petal texture.*—Glabrous.

*Petal color.*—Light pink when young, (RHS Red Purple Group 65 B), and darkening with advancing senescence and exposure to sunlight to a medium to dark pink (RHS Red Purple Group 65 A).

*Fragrance.*—Slight.

*Petal claw.*—Form. — The claw is considered truncate and has a medium-large size when compared to other varieties. Length. — Approximately 8.0 to 10.0 millimeters. Width. — Approximately 6.0 to 8.0 millimeters.

*Petal margins.*—Generally considered variable, from nearly smooth, to moderately undulate and ruffled, especially apically.

*Petal apex.*—Generally — The petal apices appear slightly domed.

*Flower pedicel.*—Length. — Considered medium-long, and having an average length of approximately 3.0 to 5.0 millimeters. Diameter. — Considered average, approximately 2.0 millimeters. Color. — A medium Green (RHS — Grey Brown Group N199 D).

*Floral nectaries.*—Color. — A dull orange-gold ((RHS Greyed Red Group 178 B).

*Calyx.*—Surface Texture. — Generally glabrous. Color. — A dull red, (approximately RHS Greyed Purple Group 183 A).

*Sepals.*—Surface Texture. — The surface has a short, fine, wooly and a gray colored texture. Size. — Average, and ovate in form. Color. — A dull red, (approximately RHS Greyed-Red Group 178 A).

*Anthers.*—Generally. — Average to above average in length. Color. — Red to reddish-orange dorsally, (approximately RHS Greyed Purple Group 179 A).

*Pollen production.*—Pollen is abundant, and has a yellow color, (approximately RHS Yellow Orange Group 17 B).

*Filaments.*—Size. — Variable in length, approximately 11.0 to 13.0 millimeters in length. Color. — White, (RHS Red Purple Group 62 D).

*Pistil.*—Number. — Usually 1, rarely 2. Generally. — Average in size. Length. — Approximately 14.0 to 16.0 millimeters including the ovary. Color .— Considered a very pale green, (approximately RHS Yellow Green Group 151 D). Surface Texture. — The variety has a long, glabrous, pale green to whitish-yellow colored pistil.

Fruit:

*Maturity when described.*—Firm ripe condition (shipping ripe); Date of first picking. — Sep. 8, 2000. Date of last picking. — Sep. 18, 2000. The date of harvest varies slightly with climatic conditions.

*Size.*—Generally — Medium large, and considered uniform.

*Average cheek diameter.*—Approximately 73.0 to 75.0 millimeters.

*Average axial diameter.*—Approximately 71.0 to 73.0 millimeters.

*Typical weight.*—Approximately 231.0 grams. This is highly dependent on cultural practices and is therefore not distinctive of the variety.

*Fruit form.*—Generally — Moderately oblate. The fruit is generally uniform in symmetry.

*Fruit suture.*—Shallow, slightly lipped, and extending from the base to the apex. No apparent callousing or stitching exists along the suture line.

*Suture.*—Color — This appears to have a yellow to golden yellow background color, (approximately RHS Yellow Orange Group 26 B) with some red orange color (approximately RHS Red Group 46 B).

*Ventral surface.*—Form — Slightly indented.

*Apex.*—Rounded.

*Base.*—Retuse.

*Stem cavity.*—Rounded too slightly enlongated in the suture plane. Average depth of the stem cavity is about 1.25 cm. Average width is about 2.51 cm.

*Fruit skin.*—Thickness. — Considered medium in thickness and tenacious to the flesh. Texture. — Glabrous. Taste. — Non-astringent. Tendency to crack. — None observed.

*Fruit skin color.* —Blush Color. — This red blush color is variable, (approximately RHS Red Orange Group 46 A to 45 B). Ground Color. — Yellow orange (approximately RHS Orange Group 26 B).

*Fruit stem.*—Medium in length, approximately 8.0 to about 9.0 millimeters. Diameter. — Approximately 2.0 to 3.0 millimeters. Color. — Pale yellow-green (approximately RHS Yellow Green Group 145 B).

*Flesh.*—Ripens. — Evenly. Texture. — Firm and dense. Fibers. — Few, small and tender. Aroma. — Very slight. Eating Quality. — Good. Flavor.— Considered sweet and mildly acidic. The flavor is considered both pleasant and balanced. Juice. — Moderate. Brix. — 11.0 degrees. Varies slightly with the number of fruit per tree, cultural practices, and climatic conditions. Flesh Color. — Yellow, (approximately RHS Yellow Orange Group 22A).

Stone:

*Type.*—Clingstone.

*Size.*—Considered medium for the variety.

*Length.*—Average about 22.0 to 24.0 millimeters.

*Width.*—Average about 21.0 to 22.0 millimeters.

*Diameter.*—Average about 18.0 to 19.0 millimeters.

*Form.*—Obovoid.

*Base.*—The stone is usually rounded, but it varies from rounded to straight.

*Apex.*—Shape. — The stone apex is raised and has an acute, short, tip.

*Stone surface.*—Surface Texture — Irregularly furrowed toward the apex, and pitted toward the base. The stone exhibits substantial pitting laterally. Substantial grooving over the apical shoulders is evident. Surface pitting is prominent generally, and more frequently, it is present basally. One long furrow on each side of suture will normally be found. Ridges. — Surface texture varies from sharp to rounded. Ventral Edge. — Width — Considered medium, and having a dimension of approximately 5 to 6.5 millimeters at the mid-suture. The wings are most prominent over the basal area. Dorsal Edge. — Shape. — Full, heavily grooved, and having jagged edges. The dorsal edge is moderately eroded over the apical shoulder.

*Stone color.*—The color of the dry stone is a light to medium brown, (approximately RHS Greyed Orange Group 166 B).

*Tendency to split.*—Few but very infrequent splitting noted.

*Kernel.*—Size.— Length — 17.0 mm. Width — 12.0 mm. Thickness — 3.0 millimeters. Form. — Obovoid. Pellicle. — Pubescent. Color .— (RHS Greyed Orange Group 173 B).

*Use.*—The subject variety 'Burnectfour' is considered to be a Nectarine of the late-season maturity, and which produces fruit which are very firm, attractively colored, and which are useful for both local and long distance shipping.

*Keeping quality.*—Excellent. Fruit has stored well up to 21 days after harvest at 1.0 degree Celsius.

*Shipping quality.*—Good. Fruit of the present variety showed minimal bruising of flesh or skin damage after normal harvest and packing procedures.

*Resistance to insects and disease.*—No particular susceptibilities were noted. The present variety has not been subjected to testing to determine any susceptibilities or resistances to known plant and or fruit diseases.

Although the new variety of nectarine tree possesses the described characteristics when grown under the ecological conditions prevailing near Fowler, Calif., in the Central part of the San Joaquin Valley of California, it will be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by Plant Letters Patent is:

1. A new distinct variety of nectarine tree substantially as illustrated and described and which is characterized principally as novelty by producing an attractively colored yellow-fleshed clingstone nectarine which is mature for harvesting and shipment approximately September 8 to September 18 under the ecological conditions prevailing in the San Joaquin Valley of Central California.

* * * * *

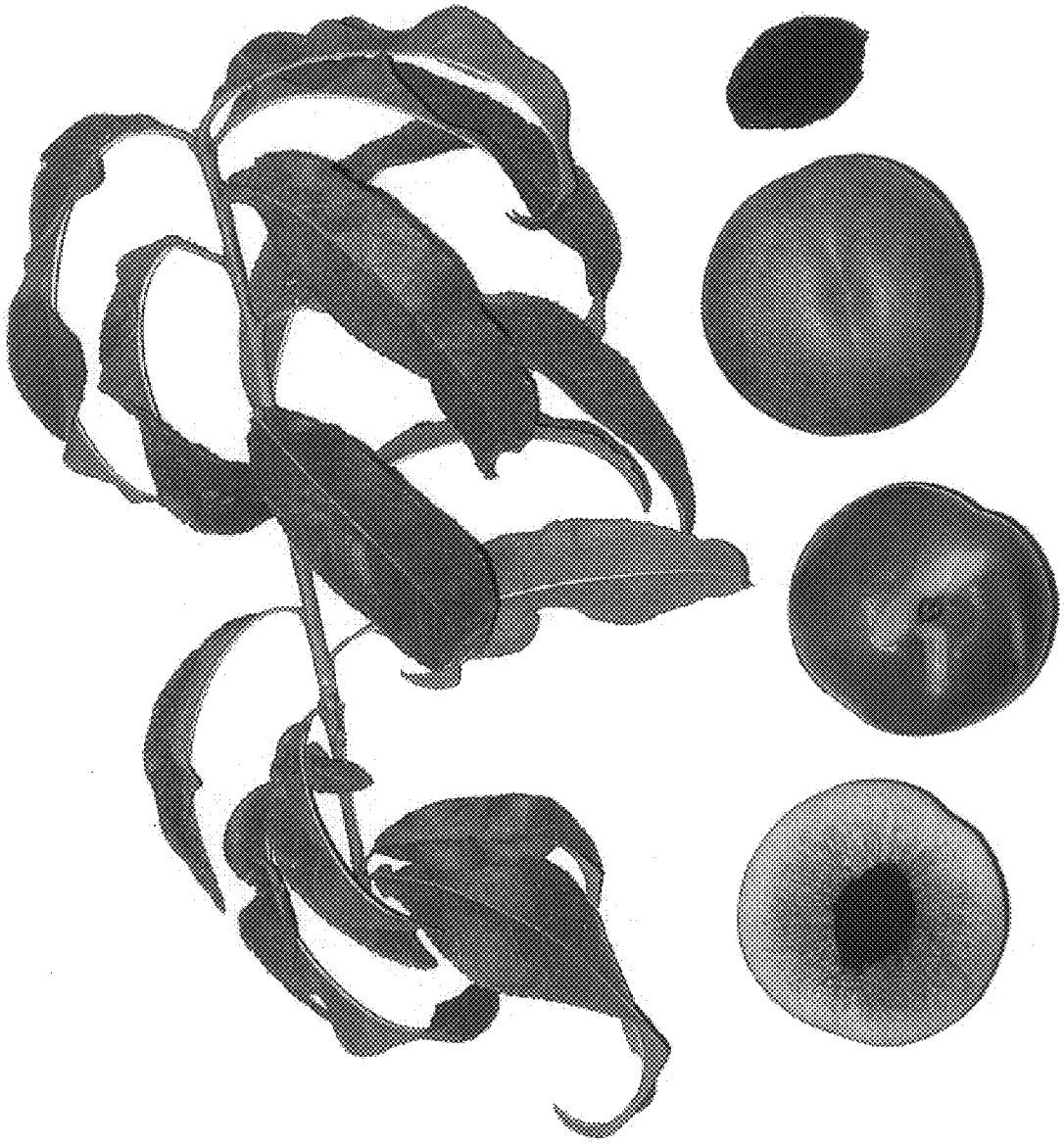

UNITED STATES PATENT AND TRADEMARK OFFICE

CERTIFICATE OF CORRECTION

PATENT NO. : PP13.477 P2
DATED : January 14, 2003
INVENTOR(S) : John K. Slaughter et al.

It is certified that error appears in the above-identified patent and that said Letters Patent is hereby corrected as shown below:

Column 2,
Line 5, replace “red color,” with -- red skin color, --.

Column 3,
Line 38, replace “177 A.” with -- 177 A). --.
Line 63, replace “current growth” with -- current season growth --.

Column 4,
Line 55, replace “at full is” with -- at full bloom is --.

Signed and Sealed this

Eleventh Day of November, 2003

JAMES E. ROGAN
*Director of the United States Patent and Trademark Office*